(12) United States Patent
Kim (10) Patent No.: US 8,843,382 B2
(45) Date of Patent: Sep. 23, 2014

(54) SYSTEM FOR PROVIDING CLINICAL INFORMATION IN REAL TIME, METHOD FOR PROVIDING CLINICAL INFORMATION IN REAL TIME, AND STORAGE MEDIUM ON WHICH A PROGRAM PERFORMING SAME IS RECORDED

(75) Inventor: Nam Ju Kim, Seoul (KR)

(73) Assignee: Medinbiz Co. Ltd., Seoul (KR)

( * ) Notice: Subject to any disclaimer, the term of this patent is extended or adjusted under 35 U.S.C. 154(b) by 0 days.

(21) Appl. No.: 14/009,161

(22) PCT Filed: Aug. 11, 2011

(86) PCT No.: PCT/KR2011/005873
§ 371 (c)(1),
(2), (4) Date: Oct. 1, 2013

(87) PCT Pub. No.: WO2012/141386
PCT Pub. Date: Oct. 18, 2012

(65) Prior Publication Data
US 2014/0067422 A1 Mar. 6, 2014

(30) Foreign Application Priority Data
Apr. 15, 2011 (KR) .................. 10-2011-0035103

(51) Int. Cl.
*G06Q 50/10* (2012.01)
*G06F 19/00* (2011.01)
*G06Q 10/10* (2012.01)
*G06Q 50/24* (2012.01)

(52) U.S. Cl.
CPC .............. *G06F 19/321* (2013.01); *G06Q 10/10* (2013.01); *G06Q 50/24* (2013.01)

USPC ................................................. 705/2

(58) Field of Classification Search
CPC ............................. G06Q 50/22–50/24
See application file for complete search history.

(56) References Cited

U.S. PATENT DOCUMENTS

| | | | |
|---|---|---|---|
| 7,520,419 B2 * | 4/2009 | Libin et al. ............. | 235/375 |
| 8,521,561 B2 * | 8/2013 | Sasai et al. ............. | 705/3 |
| 2001/0032101 A1 | 10/2001 | Statius Muller | |
| 2002/0169637 A1 * | 11/2002 | Akers et al. ............. | 705/3 |

(Continued)

FOREIGN PATENT DOCUMENTS

| | | |
|---|---|---|
| KR | 10-2003-0018208 A | 3/2003 |
| KR | 20-0310313 Y1 | 4/2003 |
| WO | 2008-103172 A1 | 8/2008 |

OTHER PUBLICATIONS

Three dimensional ultrasound (http://web.archive.org/web/20050818160423/http://web.tiscali.it/eco3d.naples-wolit/eng/preview1.htm). Obtained on Aug. 18, 2005.*

*Primary Examiner* — Sind Phongsvirajati
*Assistant Examiner* — Jonathan K Ng
(74) *Attorney, Agent, or Firm* — Novick, Kim & Lee, PLLC; Sang Ho Lee (57) ABSTRACT

The present invention relates to a system for providing clinical information in real time, to a method for providing clinical information in real time, and to a storage medium on which a program performing same is recorded. According to the present invention, the advantage of providing ultrasonic images of an unborn child in real time without an additional storage medium is that the level of clinical service provided to a pregnant woman and her family can be improved.

16 Claims, 5 Drawing Sheets

(56) References Cited

U.S. PATENT DOCUMENTS

| | | |
|---|---|---|
| 2004/0068170 A1* | 4/2004 | Wang et al. .................... 600/407 |
| 2005/0021400 A1* | 1/2005 | Postrel ........................... 705/14 |
| 2005/0038872 A1 | 2/2005 | Ono et al. |
| 2007/0125844 A1* | 6/2007 | Libin et al. .................... 235/380 |
| 2007/0138253 A1* | 6/2007 | Libin et al. .................... 235/375 |
| 2009/0030723 A1* | 1/2009 | Buchanan ........................ 705/2 |
| 2009/0240150 A1* | 9/2009 | Wang et al. .................... 600/443 |
| 2010/0228721 A1* | 9/2010 | Mok et al. ..................... 707/711 |

* cited by examiner

SYSTEM FOR PROVIDING CLINICAL INFORMATION IN REAL TIME, METHOD FOR PROVIDING CLINICAL INFORMATION IN REAL TIME, AND STORAGE MEDIUM ON WHICH A PROGRAM PERFORMING SAME IS RECORDED

TECHNICAL FIELD

The present invention relates to a system for providing clinical information in real time, a method for providing clinical information in real time, and a storage medium on which a program to perform the same is recorded. More particularly, the present invention relates to a system for providing clinical information in real time and a method for providing clinical information in real time that may provide in real time clinical information, such as electronic medical record (EMR) of a pregnant woman and an ultrasound animation of an embryo or fetus, through a portable terminal or a computer, and a storage medium on which a program to perform the same is recorded.

BACKGROUND ART

In a related art, only a copy of photograph of an embryo or fetus was the examination result that a pregnant woman has been provided with after photographing an ultrasound image of the embryo or fetus.

Currently, with the development in medical technology, many hospitals digitalize an ultrasound animation of an embryo or fetus, records the digitalized ultrasound animation on a storage medium such as a compact disc (hereinafter, referred to as a "CD"), and provides the CD to a pregnant woman.

However, to view the ultrasound image of the embryo or fetus, an electronic device, such as a computer, cable of recognizing the CD storing the ultrasound image and playing contents included in the CD was required.

Meanwhile, the pregnant woman and her family may search for information associated with a growth of an embryo or fetus in order to determine whether her embryo or fetus is growing well based on pregnancy week number, that is, week of gestation. In this case, such information is generally obtained through books or the Internet.

However, it is not easy for the pregnant woman or her family to search for the average embryonic or fetal information suitable for the corresponding week of gestation of the embryo or fetus. In addition, a significant amount of time is used.

DISCLOSURE OF INVENTION

Technical Goals

An aspect of the present invention provides a system for providing clinical information in real time and a method for providing clinical information in real time that may provide in real time average embryonic or fetal information according to corresponding week of gestation together with an ultrasound animation of an embryo or fetus, without using a separate storage medium such as a CD, and a storage medium on which a program to implement the same is recorded.

Technical Solutions

The present invention provides a system for providing clinical information in real time, the system including: a hospital server configured to allocate unique code information to input clinical information and thereby store the input clinical information, and to output a code pattern corresponding to the code information; a terminal configured to read the output code pattern and thereby extract the code information; and a central server including an information extraction unit configured to extract, from the hospital server, clinical information to which the same code information as the code information extracted by the terminal is allocated, and to transmit the extracted clinical information to the terminal.

The hospital server may include: a clinical information collection unit configured to receive the clinical information; a code information allocation unit configured to allocate the unique code information to the input clinical information; and a clinical information database (DB) configured to store the clinical information to which the code information is allocated.

Also, the terminal may include: a camera module configured to photograph the code pattern and thereby create an electronic image of the code pattern; a code reader configured to read the electronic image of the code pattern and thereby extract the code information allocated to the code pattern; and an image processing unit configured to display, on a screen, the clinical information received from the information extraction unit.

Also, the clinical information may include electronic medical record (EMR) data of a pregnant woman including at least one set of data among a medical history, a family history, an age, a height, a weight, a blood type, a degree of obesity, a surgery record, a birth record, and a dosage record about the pregnant woman, or ultrasound data including at least one set of data among a height, a weight, a head circumference, and an ultrasound animation about an embryo or fetus.

Also, the hospital server may further include a code reader configured to recognize the code pattern and thereby extract the code information allocated to the code pattern. The code information allocation unit may allocate, to the clinical information, the code information extracted by the code reader.

Also, the clinical information collection unit may convert, to a predetermined data format, the EMR data of the pregnant woman and the ultrasound data that are provided in different data formats.

Also, the clinical information collection unit may receive metadata about gestational age information and may add the received metadata to the ultrasound data. The central server may further include: a standard embryonic or fetal information DB configured to store ultrasound animation samples for each week of gestation of the embryo or fetus indicating an average growth state; and an embryonic or fetal information matching unit configured to receive the ultrasound data extracted by the information extraction unit, and thereby extract the metadata, and configured to extract, from the standard embryonic or fetal information DB, an ultrasound animation sample corresponding to the gestational age information of the extracted metadata and thereby transmit the extracted ultrasound animation sample to the terminal.

Also, the code pattern may be printed on a sonogram of the embryo or fetus that is output as a printing material or a medical card including personal information of the pregnant woman, which is required for a hospital practice.

Also, the image processing unit may be configured to overlay and thereby display the ultrasound animation sample on an image of the sonogram obtained by the camera module.

Also, the medical card may store mileage information used to utilize a service designated at an affiliated store.

Also, the present invention provides a method for providing clinical information in real time, the method including: a)

allocating, by a hospital server, unique code information to input clinical information to store the input clinical information, and outputting a code pattern corresponding to the code information; b) reading, by a terminal, the output code pattern to extract the code information; and c) extracting, by an information extraction unit included in a central server from the hospital server, clinical information to which the same code information as the code information extracted by the terminal is allocated, and transmitting the extracted clinical information to the terminal.

The a) may include: a1) receiving, by a clinical information collection unit included in the hospital server, the clinical information; a2) allocating, by a code information allocation unit included in the hospital server, the unique code information to the input clinical information; a3) storing, in a clinical information DB, the clinical information to which the code information is allocated; and a4) outputting, an output unit included in the hospital server, the code pattern including the code information.

Also, the b) may include: b1) photographing, by a camera module included in the terminal, the code pattern to create an electronic image of the code pattern; and b2) reading, by a code reader included in the terminal, the electronic image of the code pattern to extract the code information allocated to the code pattern.

Also, the present invention provides a computer-readable storage medium storing a program to implement the method for providing clinical information in real time.

Effects of Invention

According to embodiments of the present invention, an ultrasound animation of an embryo or fetus may be provided in real time without using a separate storage medium and thus, it is possible to improve a level of a medical treatment service for a pregnant woman and her family.

Also, average embryonic or fetal information according to current week of gestation of an embryo or fetus may be provided in real time to the pregnant woman and her family together with an ultrasound animation of the embryo or fetus, thereby enabling the pregnant woman and her family to intuitively determine a current growth state of the embryo or fetus.

BEST MODE FOR CARRYING OUT THE INVENTION

Hereinafter, exemplary embodiments of the present invention will be described with reference to the accompanying drawings. Initially, it should be noted that like reference numerals refer to like constituent elements although they are illustrated in different drawings. Also, when a predetermined detailed description is determined to make the purpose of the present invention unnecessarily ambiguous, the predetermined detailed description will be omitted. Further, hereinafter, exemplary embodiments of the present invention will be described, but the technical spirit of the present invention is not limited thereto or restricted thereby and may be carried out by those skilled in the art.

Figure 1:
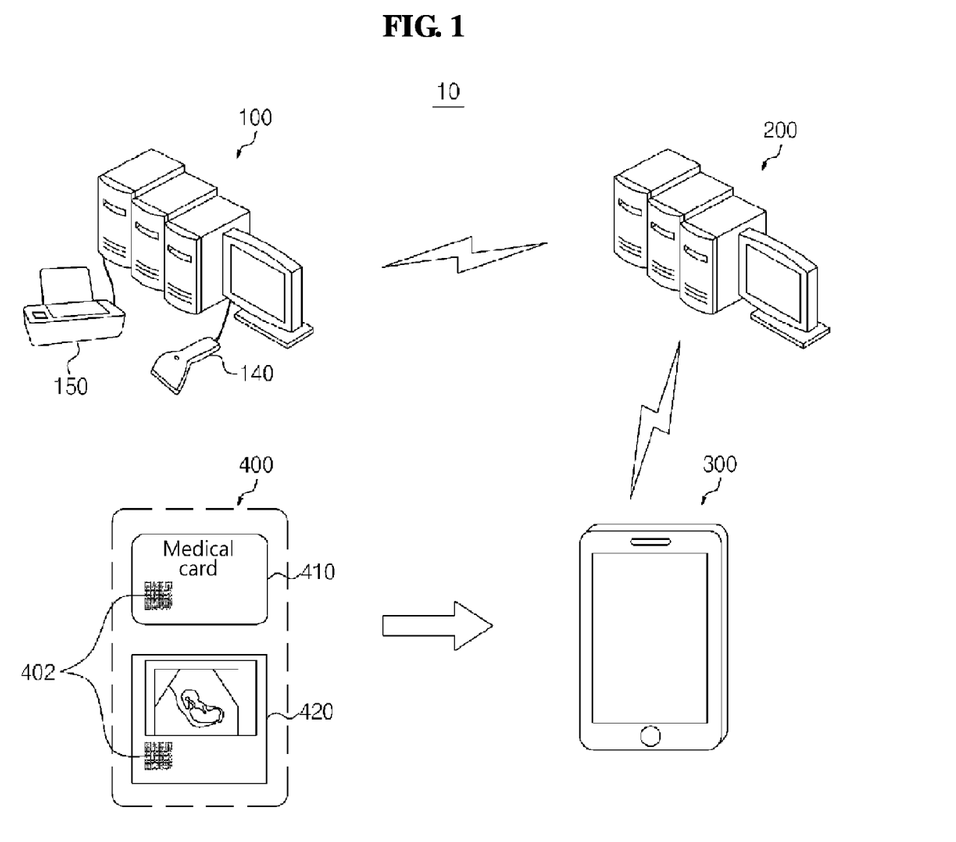
FIG. 1 is a diagram illustrating a system for providing clinical information in real time according to an exemplary embodiment of the present invention.
Figure 2:
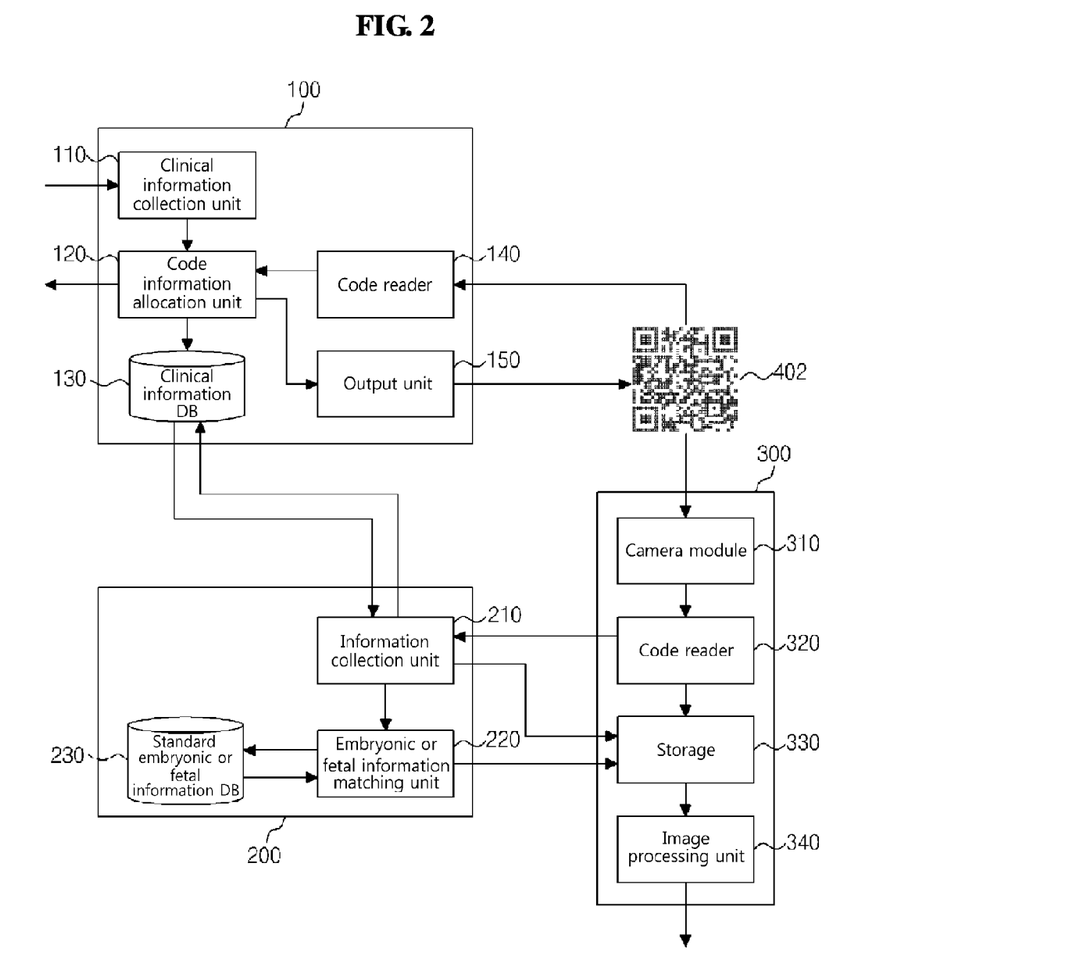
FIG. 2 is a block diagram illustrating a system for providing clinical information in real time according to an exemplary embodiment of the present invention.

FIG. 1 is a diagram illustrating a system for providing clinical information in real time according to an exemplary embodiment of the present invention, and FIG. 2 is a block diagram illustrating a system for providing clinical information in real time according to an exemplary embodiment of the present invention.

Hereinafter, a system 10 for providing clinical information in real time according to an exemplary embodiment of the present invention will be described with reference to FIGS. 1 and 2.

Here, clinical information may include electronic medical record (EMR) data of a pregnant woman, that is, an EMR including data such as a medical history, a family history, an age, a height, a weight, a blood type, a degree of obesity, a surgery record, a birth record, and a dosage record about the pregnant woman, and ultrasound data including data, such as a height, a weight, a head circumference, and an ultrasound animation about an embryo or fetus.

Such EMR data of the pregnant woman and ultrasound data about the embryo or fetus may be basic materials used to determine heath states of the pregnant woman and the embryo or fetus and thus, may be used on a side of a doctor to provide an appropriate medical service to the pregnant woman and the embryo or fetus and may be used on a side of the pregnant woman and her family to verify a state of the embryo or fetus invisible with bare eyes The system 10 for providing clinical information in real time according to an exemplary embodiment of the present invention may provide in real time clinical information, particularly, ultrasound data such as an ultrasound animation of the embryo or fetus to the pregnant woman and her family so as to be capable of easily verifying a growth state of the embryo or fetus.

To this end, the system 10 for providing clinical information in real time according to an exemplary embodiment of the present invention includes a hospital server 100, a central server 200, a terminal 300, and a code recording medium 400.

The hospital server 100 allocates unique code information to input clinical information to store the input clinical information, and outputs a code pattern 402 corresponding to the code information Specifically, the hospital server 100 includes a clinical information collection unit 110, a code information allocation unit 120, a clinical information database (DB) 130, a code reader 140, and an output unit 150.

The clinical information collection unit 110 receives clinical information including collected EMR data of the pregnant woman and ultrasound data of the embryo or fetus obtained using an ultrasound diagnostic device.

Here, the clinical information may be EMR of another hospital at which the pregnant woman has received a medical treatment. A data format of EMR may differ for each hospital and thus, may be incompatible with another data format, which also applies alike to the ultrasound data of the embryo or fetus.

To make clinical information having a different data format available on a system, the clinical information collection unit 110 converts, to a predetermined data format, the EMR data of the pregnant woman and the ultrasound data that are provided in different data formats.

Accordingly, clinical information of a plurality of hospitals at which the pregnant women has received a medical treatment may be integrated and thus, information on the pregnant woman and the embryo or fetus may be provided.

The clinical information collection unit 110 receives metadata about gestational age information and adds the received metadata to the clinical information, particularly, the ultrasound data.

The metadata may be recorded based on a unit indicating a gestational period, such as a time, a day, a week, and a month. For example, data indicating the week of gestation, such as the first week of gestation, the second week of gestation, the third week of gestation, and the like, may be added to the clinical information.

The metadata added to the clinical information is used to provide the pregnant woman and her family with embryonic or fetal information according to the corresponding week of gestation, which will be described later.

The clinical information and the metadata may be input through an input operation of a doctor or a manager of the hospital server 100, or may be automatically input through ultrasound diagnostic equipment or a DB interacting with the clinical information collection unit 110.

The code information allocation unit 120 allocates the unique code information to the clinical information received by the clinical information collection unit 110.

The clinical information DB 130 stores the clinical information to which the code information is allocated.

The code reader 140 recognizes the code pattern 402 and extracts the code information allocated to the code pattern 402. Here, the code information allocation unit 120 allocates the code information extracted by the code reader 140 to the clinical information transferred from the clinical information collection unit 110.

Accordingly, clinical information on the same pregnant woman may be continuously accumulated and stored.

The output unit 150 prints the code pattern 402 including the code information on a printed material or displays the code pattern 402 on a screen of a display device such as a monitor.

The code pattern 402 output by the output unit 150 may be printed on the code recording medium 400 in a form such as a medical card 410 including personal information of the pregnant woman, which is required for a hospital practice, and a sonogram 420 of the embryo or fetus output as a printed material.

Accordingly, using the code recording medium 400 and the terminal 300 that the pregnant woman and her family can conveniently carry, the pregnant woman and her family may be provided with clinical information in real time.

Meanwhile, the medical card 410 may be configured in a form of an electronic card storing mileage information used to utilize a service designated at an affiliated store, so as to be capable of simultaneously performing a functionality of a membership card.

The code pattern 402 output by the output unit 150 may be configured in a form of a one-dimensional code such as a barcode, or a two-dimensional code such as a quick response (QR) code, a micro QR code, a PDF417 code, a Data Matrix code, Maxi code, vericode, cadablock code, aztec code, a calula code, BP04 State code, and Postnet code.

The central server 200 includes an information collection unit 210, an embryonic or fetal information matching unit 220, and a standard embryonic or fetal information DB 230.

The information collection unit 210 extracts, from the clinical information DB 130 of the hospital server 100, clinical information to which the same code information as the code information extracted by a code reader 320 of the terminal 300 from the code pattern 402 is allocated, and transmits the extracted clinical information to a storage 330 or an image processing unit 340 of the terminal 300.

The embryonic or fetal information matching unit 220 receives the clinical information extracted by the information extraction unit 210 and thereby extracts the metadata added to the clinical information, and extracts, from the standard embryonic or fetal information DB 230, an ultrasound animation sample corresponding to the gestational age information of the extracted metadata and thereby transmits the extracted ultrasound animation sample to the storage 330 or the image processing unit 340 of the terminal 300.

To this end, the standard embryonic or fetal information DB 230 is provided and stores ultrasound animation samples for each week of gestation of the embryo or fetus indicating an average growth state.

Figure 3:
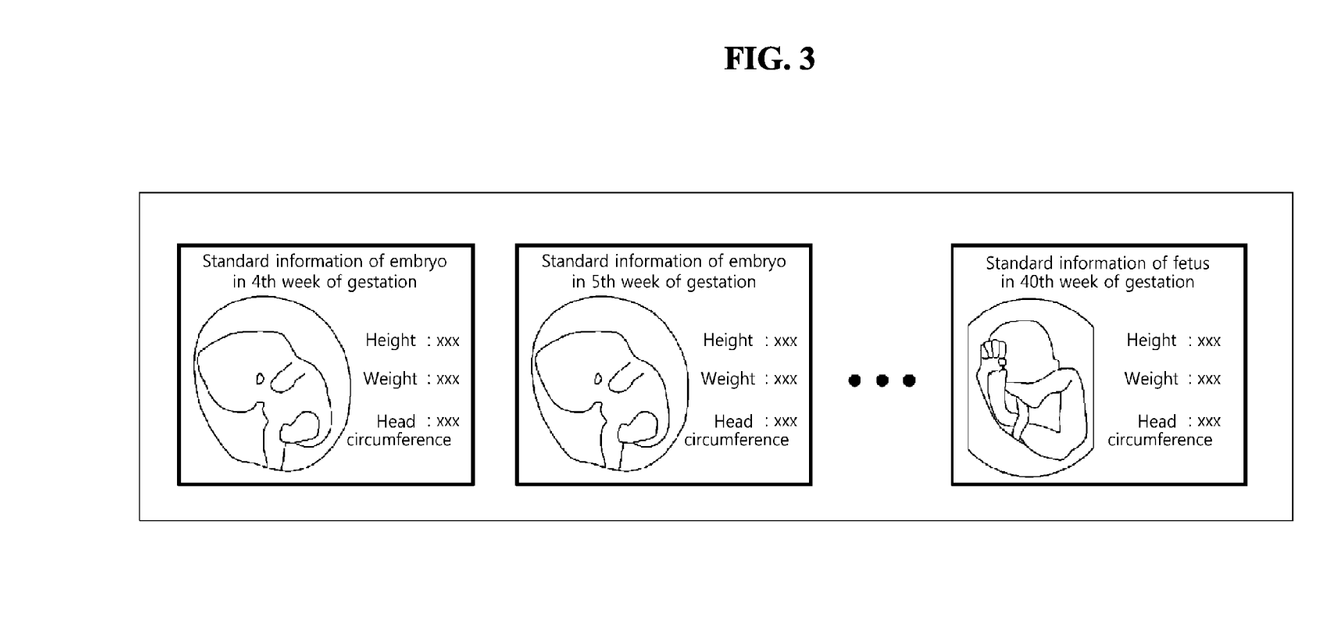
FIG. 3 illustrates an example of ultrasound animation samples for each week of gestation of an embryo or fetus.

FIG. 3 illustrates an example of ultrasound animation samples for each week of gestation of an embryo or fetus.

As illustrated in FIG. 3, ultrasound animation samples stored in the standard embryonic or fetal information DB 230 are classified and thereby stored for each week of gestation. The embryonic or fetal information matching unit 220 extracts an ultrasound animation sample of a week of gestation close to a week of gestation corresponding to gestational age information of metadata.

For example, when a pregnant woman in the fifth week of gestation receives a medical treatment and corresponding clinical information is input to the clinical information collection unit 110, the clinical information collection unit 110 adds metadata corresponding to the fifth week of gestation to the clinical information.

The embryonic or fetal information matching unit 220 analyzes the metadata of the clinical information received from the information extraction unit 210, extracts the ultrasound animation sample corresponding to the fifth week of gestation, and transmits the extracted ultrasound animation sample to the terminal 300.

As described above, the terminal 300 reads the code pattern 402 output by the output unit 150 to thereby extract code information and display, on a screen, the clinical information received from the central server 200.

To this end, the terminal 300 includes a camera module 310, the code reader 320, the storage 330, and the image processing unit 340.

The camera module 310 photographs the code pattern 402 printed on the code recording medium 400, such as the medical card 410 or the sonogram 420, to thereby create an electronic image of the code pattern 402.

The camera module 310 may be configured as a digital imaging device including a charge-coupled device (CCD) sensor or a complementary metal-oxide semiconductor (CMOS) sensor.

The code reader 320 reads the electronic image of the code pattern 402 created by the camera module 310, and extracts the code information allocated to the code pattern 402.

The storage 330 stores the clinical information received from the information extraction unit 210 and the ultrasound animation sample received from the embryonic or fetal information matching unit 220.

The image processing unit 340 displays the received clinical information on the screen included in the terminal 300.

Also, the image processing unit 340 overlays and thereby displays the ultrasound animation sample on an image of the code recording medium 400 obtained by the camera module 310. To this end, a program to achieve an augmented reality may be embedded within the image processing unit 340.

Figure 4:
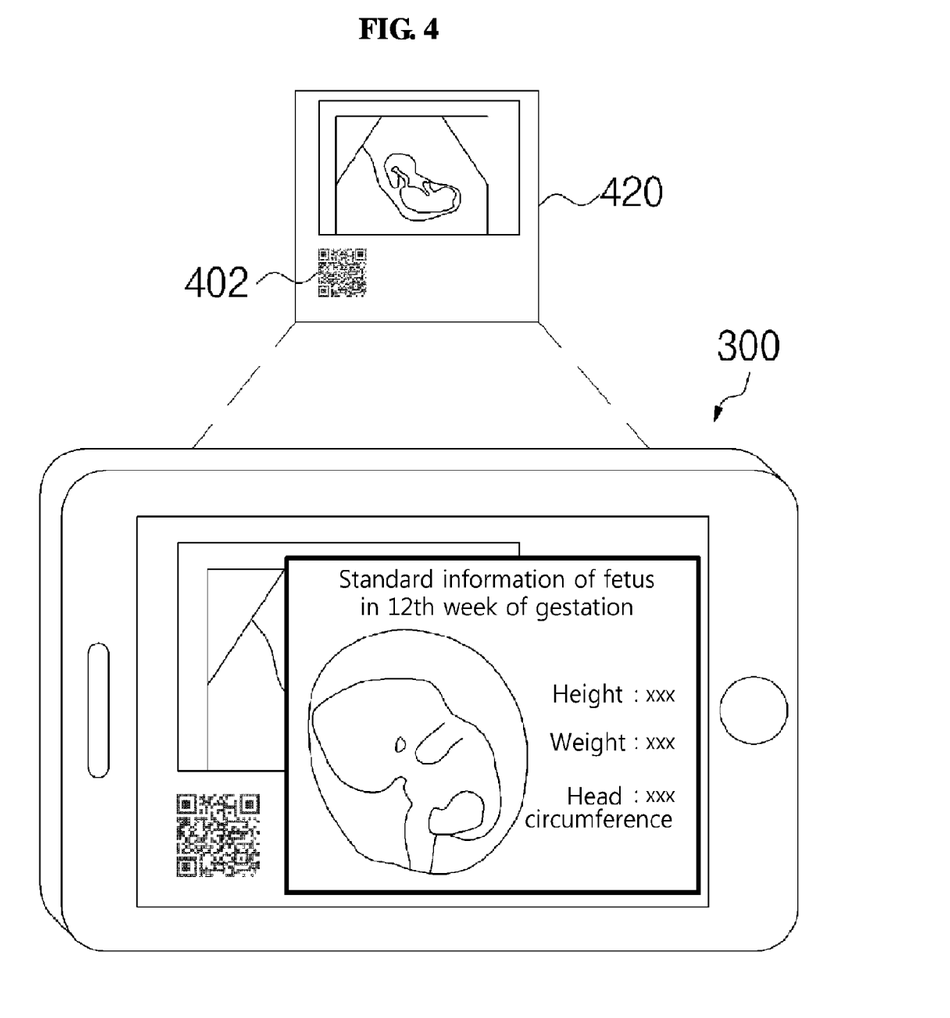
FIG. 4 illustrates an example of an ultrasound animation sample overlaid and thereby displayed on an image of a sonogram.

FIG. 4 illustrates an example of an ultrasound animation sample overlaid and thereby displayed on an image of a sonogram.

As illustrated in FIG. 4, the image processing unit 340 may express, using an augmented reality, an image of an ultrasound animation sample on an image of the sonogram 420 photographed by the camera module 310.

Here, the ultrasound animation sample may be overlaid using a see-through scheme so as to simultaneously view the sonogram 420 and the ultrasound animation sample.

By displaying, on the sonogram 420, an ultrasound animation sample of an embryo or fetus corresponding to the same week of gestation as a week of gestation of a conceived embryo or fetus and indicating the average growth state, the pregnant woman and her family may intuitively verify the growth state of the embryo or fetus.

Here, by including, in the ultrasound animation sample, general embryonic or fetal text information such as a height, a weight, and a head circumference of the embryo or fetus indicating the average growth state, the pregnant woman and her family may become aware of a growth of the conceived embryo or fetus compared to an average embryonic or fetal growth level.

The terminal 300 may be configured in a variety of types that may include the aforementioned constituent elements. For example, the terminal 300 may be configured as a portable device, such as a smart phone, a mobile communication terminal, a personal digital assistant (PDA), and a notebook.

Figure 5:
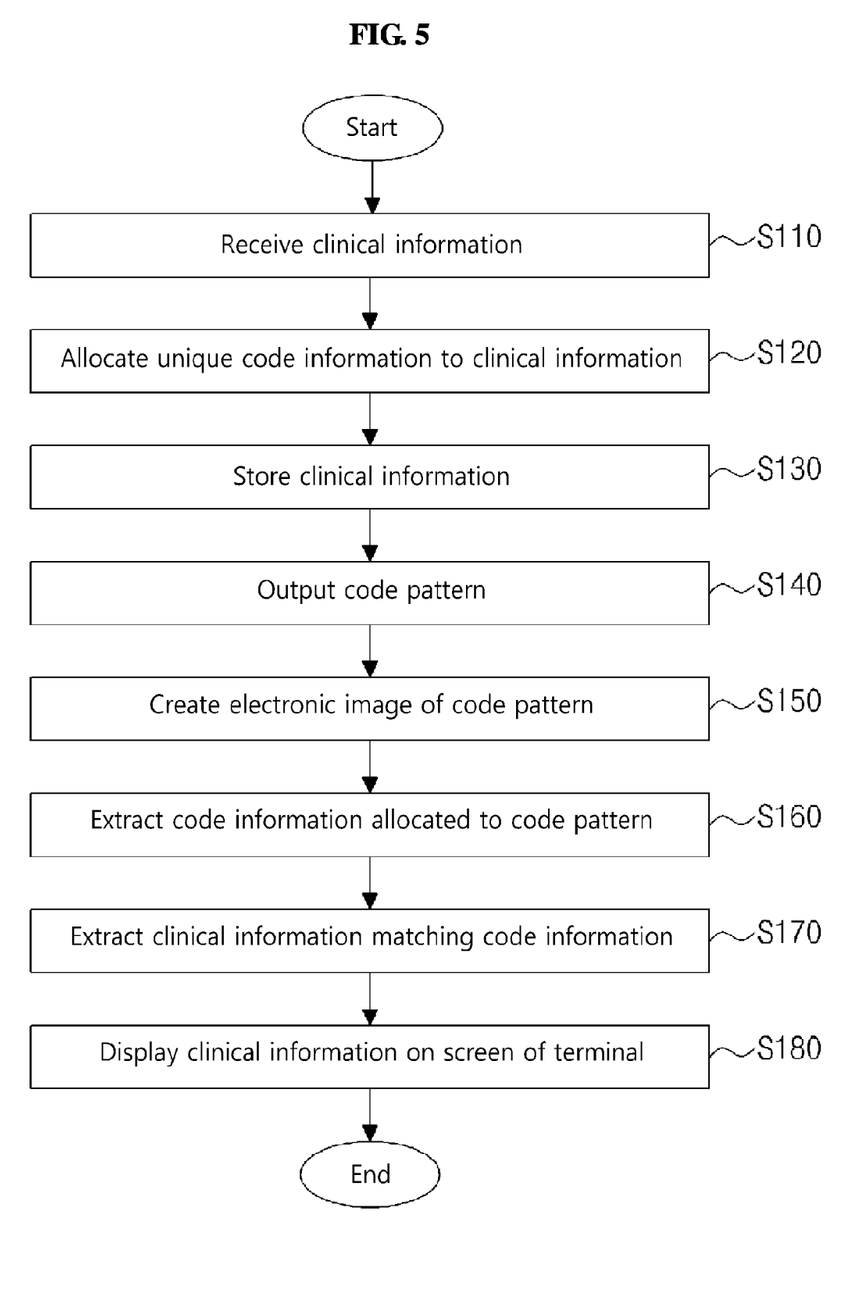
FIG. 5 is a flowchart illustrating a method for providing clinical information in real time according to an exemplary embodiment of the present invention.

FIG. 5 is a flowchart illustrating a method for providing clinical information in real time according to an exemplary embodiment of the present invention.

Hereinafter, a process of providing clinical information in real time using the system 10 for providing clinical information in real time according to an exemplary embodiment of the present invention will be described with reference to FIG. 5.

In operation S110, the clinical information collection unit 110 receives clinical information that is input through an input operation of a doctor or a manager of the hospital server 100 or automatically input through ultrasound diagnostic equipment or a DB interacting with the clinical information collection unit 110.

Here, as described above, the clinical information collection unit 110 may add metadata to the clinical information.

In operation S120, the code information allocation unit 120 allocates unique code information to the clinical information. In operation S130, the clinical information to which the code information is allocated is stored in the clinical information DB 130.

In operation S140, the output unit 150 outputs the code pattern 402 including the same code information as the code information allocated to the clinical information. The output code pattern 402 may be printed on the code recording medium 400 such as the medical card 410 or the sonogram 420.

In operation S150, the camera module 310 included in the terminal 300 photographs the code pattern 402 printed on the code recording medium 400 and thereby creates an electronic image of the code pattern 402. In operation S160, the code reader 320 reads the electronic image of the code pattern 402 and thereby extracts code information allocated to the code pattern 402.

In operation S170, the information extraction unit 210 included in the central server 200 extracts, from the clinical information DB 130 of the hospital server 100, clinical information to which the same code information as the code information extracted by the code reader 320 is allocated, and transmits the extracted clinical information to the terminal 300.

In operation S180, the image processing unit 340 of the terminal 300 displays the received clinical information on the screen included in the terminal 300.

As described above, using the system 10 for providing clinical information in real time, it is possible to accumulatively store clinical information on the same pregnant woman, to extract an ultrasound animation sample, and to overlay and thereby display the extracted ultrasound animation sample on an image of a sonogram. The aforementioned process may also be selectively performed in such a manner that a user receives a control signal through a user interface preconfigured in the terminal 300.

Meanwhile, the method for providing clinical information in real time according to the present invention may be recorded in computer-readable media as a computer-readable code. The computer-readable media may include any type of storage devices on which data readable by a computer system is recorded. Examples of computer-readable media may include read-only memory (ROM), random access memory (RAM), CD-ROM, magnetic tape, floppy disks, and optical data storage devices, and the like. Also, the computer-readable media may include a form of a carrier wave, for example, transmission through the Internet. Also, the computer-readable media may be distributed over a computer system connected to a network and a computer-readable code may be stored and executed using a distributive scheme. Functional programs, codes, and code segments to configure the present invention may be easily inferred by programmers in the art.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A system for providing clinical information in real time, the system comprising:

a hospital server comprising:
a clinical information collection unit configured to receive clinical information from at least one of medical personnel, hospital server personnel, a device, and database,
a code information allocation unit configured to allocate code information to the clinical information, and a clinical information database (DB) configured to store the clinical information to which the code information is allocated, and wherein the hospital server outputs a code pattern corresponding to the code information;

a terminal comprising:
a camera module configured to photograph the code pattern and create an electronic image of the code pattern,
a code reader configured to read the electronic image of the code pattern and extract the code information from the code pattern, and
an image processing unit configured to display the received clinical information on a screen, wherein the terminal is configured to be used by a patient; and a central server comprising:
an information extraction unit configured to extract the clinical information to which the code information is assigned from the hospital server, and to transmit the clinical information to the terminal;

wherein the clinical information comprises ultrasound data and electronic medical record (EMR) data of the patient, and the clinical information collection unit receives metadata of gestational age information and adds the received metadata to the ultrasound data;

wherein the image processing unit overlays and displays an ultrasound animation sample on an image of a sonogram obtained by the camera module at the terminal, and wherein the terminal is a mobile communication device; and wherein the ultrasound animation sample is overlaid on the sonogram image obtained by the camera module using a see-through display so as to provide a simultaneous view of the sonogram image and the ultrasound animation sample to the patient.

2. The system of claim 1, wherein the central server further comprises:

a standard embryonic or fetal information DB configured to store ultrasound animation samples for each week of gestation of an embryo or fetus indicating an average growth state; and an embryonic or fetal information matching unit:

configured to receive the ultrasound data extracted by the information extraction unit and to extract the metadata from the ultrasound data, and configured to extract the ultrasound animation sample from the standard embryonic or fetal information DB corresponding to the gestational age information of the metadata and to transmit the extracted ultrasound animation sample to the terminal.

3. The system of claim 2, wherein the clinical information collection unit converts and integrates the clinical information that includes the ultrasound data and the EMR data of the patient in a different format from different hospitals into a predetermined data format, wherein the EMR data of a patient comprise at least one of an age, a height, a weight, a blood type, a degree of obesity, a surgery record, a birth record, and a dosage record of the patient, and wherein the ultrasound data comprises at least one of a height, a weight, a head circumference, and an ultrasound animation of the embryo or fetus.

4. The system of claim 1, wherein the clinical information collection unit converts and integrates the clinical information that includes the ultrasound data and the EMR data of the patient in a different format from different hospitals into a predetermined data format, wherein the EMR data of patient comprise at least one of an age, a height, a weight, a blood type, a degree of obesity, a surgery record, a birth record, and a dosage record of the patient, and wherein the ultrasound data comprises at least one of a height, a weight, a head circumference, and an ultrasound animation of the embryo or fetus.

5. The system of claim 4, wherein the hospital server further comprises:

a code reader configured to recognize the code pattern and extract the code information allocated to the code pattern, wherein the code information allocation unit allocates the code information extracted by the code reader to the clinical information, wherein the code pattern is printed on the sonogram of the embryo or fetus on a printing material or a medical card that includes personal information of the patient for a medical treatment, wherein the patient is a pregnant woman.

6. The system of claim 1, wherein the medical card includes mileage information which is available to be used at an affiliated store.

7. The system of claim 1, wherein the image processing unit is configured so that the image of the ultrasound animation sample and the sonogram image obtained by the camera module are visually displayed in an augmented reality view on the terminal.

8. A method for providing clinical information in real time, the method comprising:

a) receiving code information from at least one of medical personnel, hospital server personnel, a device, and database and allocating the code information to clinical information by a hospital server so as to store the clinical information, and output a code pattern corresponding to the code information;

b) at a terminal, reading the code pattern to extract the code information; and c) at a central server, extracting clinical information to which the code information is allocated, and transmitting the extracted clinical information to the terminal, wherein the step a) comprises:

a1) receiving the clinical information at a clinical information collection unit, a2) allocating the code information to the clinical information at a code information allocation unit, a3) storing the clinical information to which the code information is allocated at a clinical information database (DB), and a4) outputting the code pattern corresponding to the code information by an output unit, wherein the clinical information comprises ultrasound data and electronic medical record (EMR) data of a patient, wherein the clinical information collection unit receives metadata of gestational age information and adds the received metadata to the ultrasound data, wherein the terminal is configured to be used by the patient;

at the terminal, displaying the clinical information through an image processing unit on a screen, wherein an ultrasound animation sample is overlaid and displayed on an image of a sonogram obtained by a camera module at the terminal, and wherein the terminal is a mobile communication device; and wherein the ultrasound animation sample is overlaid on the sonogram image obtained by the camera module using a see-through display so as to provide a simultaneous view of the sonogram image and the ultrasound animation sample to the patient.

9. The method of claim 8, wherein the step b) further comprises:

b1) photographing the code pattern by a camera module at the terminal so as to create an electronic image of the code pattern; and b2) reading the electronic image of the code pattern by a code reader at the terminal so as to extract the code information allocated to the code pattern.

10. The method of claim 9, wherein the clinical information collection unit converts and integrates the clinical information that includes the ultrasound data and the EMR data of the patient in a different format from different hospitals, wherein the EMR data of the patient comprise at least one of an age, a height, a weight, a blood type, a degree of obesity, a surgery record, a birth record, and a dosage record of the patient, and wherein the ultrasound data comprises at least one of a height, a weight, a head circumference, and an ultrasound animation of the embryo or fetus.

11. The method of claim 8, wherein the clinical information collection unit converts and integrates the clinical information that includes the ultrasound data and the EMR data of the patient in a different format from different hospitals into a predetermined data format,
- wherein the EMR data of the patient comprise at least one of an age, a height, a weight, a blood type, a degree of obesity, a surgery record, a birth record, and a dosage record of the patient, and
- wherein the ultrasound data comprises at least one of a height, a weight, a head circumference, and an ultrasound animation of the embryo or fetus.

12. The method of claim 11, wherein the hospital server further comprises a code reader,
- wherein the code reader recognizes the code pattern and extracts the code information allocated to the code pattern, and
- wherein the code information allocation unit allocates the code information extracted by the code reader to the clinical information.

13. The method of claim 11, wherein the central server further comprises an embryonic or fetal information matching unit,
- wherein the embryonic or fetal information matching unit receives the ultrasound data extracted and extracts the metadata from the ultrasound data, and
- wherein the embryonic or fetal information matching unit extracts the ultrasound animation sample corresponding to the gestational age information of the extracted metadata from a standard embryonic or fetal information DB storing ultrasound animation samples for each week of gestation of the embryo or fetus indicating an average growth state and transmits the extracted ultrasound animation sample to the terminal.

14. The method of claim 13, wherein the code pattern is printed on the sonogram of the embryo or fetus on a printing material or a medical card that includes mileage information which is available to be used at an affiliated store and personal information of the patient for a medical treatment.

15. A non-transitory computer-readable storage medium storing a program that, when executed by a computer, causes the computer to perform a process comprising:
- a) receiving code information from at least one of medical personnel, hospital server personnel, a device, and database and allocating the code information to clinical information by a hospital server so as to store the clinical information, and output a code pattern corresponding to the code information;
- b) at a terminal, reading the code pattern to extract the code information; and
- c) at a central server, extracting clinical information to which the code information is allocated, and transmitting the extracted clinical information to the terminal, wherein the step a) comprises:
- a1) receiving the clinical information at a clinical information collection unit,
- a2) allocating the code information to the clinical information at a code information allocation unit,
- a3) storing the clinical information to which the code information is allocated at a clinical information database (DB), and
- a4) outputting the code pattern corresponding to the code information by an output unit, wherein the clinical information comprises ultrasound data and electronic medical record (EMR) data of a patient, wherein the clinical information collection unit receives metadata of gestational age information and adds the received metadata to the ultrasound data;

wherein the terminal is configured to be used by the patient;

at the terminal, displaying the clinical information through an image processing unit on a screen, wherein an ultrasound animation sample is overlaid and displayed on an image of a sonogram obtained by a camera module at the terminal, and wherein the terminal is a mobile communication device; and wherein the ultrasound animation sample is overlaid on the sonogram image obtained by the camera module using a see-through display so as to provide a simultaneous view of the sonogram image and the ultrasound animation sample to the patient.

16. The non-transitory computer-readable storage medium of claim 15,
wherein the step b) comprises:
- b1) photographing the code pattern by a camera module at the terminal so as to create an electronic image of the code pattern; and
- b2) reading the electronic image of the code pattern by a code reader at the terminal so as to extract the code information allocated to the code pattern.

* * * * *